United States Patent [19]
van den Brink et al.

[11] Patent Number: 5,380,322

[45] Date of Patent: Jan. 10, 1995

[54] BONE FIXATION DEVICE

[76] Inventors: Breunis van den Brink, Harskampweg 37, 6731 AA Otterloo; Gerrit J. Termaten, Hanzeweg 17, 7241 CS, Lochem; Johannes A. de Gruijl, Wildbaan 1, 3958 DH Amerongen, all of Netherlands

[21] Appl. No.: 992,030

[22] Filed: Dec. 17, 1992

[51] Int. Cl.⁶ .............................................. A61F 5/04
[52] U.S. Cl. ........................................ 606/57; 606/53
[58] Field of Search ................... 606/53, 54, 55, 56, 606/57, 58, 59

[56] References Cited
U.S. PATENT DOCUMENTS 4,848,368  1/1989  Kronner ..................... 606/57

*Primary Examiner*—Stephen C. Pellegrino
*Assistant Examiner*—Sonya Harris
*Attorney, Agent, or Firm*—Adduci, Mastriani, Schaumberg & Schill

[57] ABSTRACT

Bone fixation device comprising a profiled bar (1) on which at least two supporting members (2) have been movably and lockably mounted. The supporting members (2) comprise a sliding portion (3) having an opening (4) therein for passing the bar (1) and a supporting plate (5) extending from the sliding part (3), with a convex and concave surface (12, 13). Against the convex surface lies a ring (15) and against the concave surface lies a convex surface (21) of a receiving element (20, 27) in which screws (23) have been clamped, which can be secured in a bone part (24). Through the ring (15) extends a bolt (7) that has been screwed into one of a number of threaded bores (19) in the receiving element (20, 27) and which bolt extends through a relatively large opening in the supporting plate (5).

16 Claims, 3 Drawing Sheets

BONE FIXATION DEVICE

BACKGROUND OF THE INVENTION

The invention relates to a bone fixation device comprising a profiled bar, on which at least two supporting members have been movably and lockably mounted, which supporting members have a sliding portion with an opening therein for passing the bar and onto which supporting members receiving elements can be clamped, each serving to receive at least one screw, which can be secured in one part of a bone.

In such a device, it is desirable that the screws, mounted in the relating bone portions, can take up various positions in relation to each other and thus need not be parallel to each other.

In the device known from EP-A-0 374 093, this is achieved through the fact that the receiving element can be rotated around a clamping bolt, which has been screwed in an intermediate block which itself is secured onto the supporting member by means of another clamping bolt. The axis of the last-mentioned clamping bolt is almost parallel to the axis of the bar.

With this known device, one can achieve a large degree of freedom in the position of the screws. However, this results in a complicated construction. By the presence of the intermediate block and the arrangement of the several parts, the device will also take up a considerable space outside of the part of the body in which the bone portions are situated. Further, the device is not very conveniently arranged for non-technical persons who will normally use such a device.

SUMMARY OF THE INVENTION

The invention now intends to remove these objections and to that end provides for, that each supporting member comprises a supporting plate extending from the sliding portion of the supporting member situated on the bar, with one surface of the supporting plate being concave and the opposing surface being convex and with an opening made in each plate for passing a clamping bolt which extends through a ring having a concave surface lying flat against the convex surface of the supporting plate and which bolt has been screwed into one of a number of threaded bores made in a receiving element having a convex surface lying flat against the concave surface of the supporting plate.

In this way, one can obtain a simple construction, which comprises few parts and in which sufficient possibilities are present for mutual adjustment of the screws to be mounted in the bone portions. Obviously, the opening through which the clamping bolt passes can have a relatively large diameter.

Further, relatively smooth surfaces are obtained, because of which bearing the device present fewer objections to the patient.

Therein, in particular the centre of curvature of the concave surface of the supporting plate will approximately come to lie in the bone portion which has to be fixedly connected to the device.

Through this, the exertion of torque on the bone can be largely avoided. With a certain adjusted distance between the supporting members, during positioning of the parts of the bone, no difference of length thereof will occur. Possible extension of the bone will be parallel to the axis thereof.

According to a further development of the invention, the supporting plate can extend from the sliding portion in such a way, that the surfaces going through the edges of the opening in the convex and concave surfaces are situated at both sides of the axis of the bar.

By this position of the supporting plate and by the direct connection of the supporting plate with the receiving element, the bar on which the supporting members have been mounted, will be able to extend close to the outwardly directed surface of the receiving elements and thus close to the part of the body in which the bone portions are situated which have to be fixated in relation to each other. Here, the outwardly directed surface of the receiving elements is understood to mean the surface from which the screws to be fitted into the bone portions protrude.

In particular, the bar will have a square cross-section and a surface, going through two longitudinal edges of the bar will extend between the convex and the concave surfaces of the supporting plate, while in the sliding portion of the supporting member a slot has been made which extends towards one of said longitudinal edges of the bar, at which the sliding portion can be clamped onto the bar by means of a bolt, with which parts of the sliding portion lying at both sides of the slot are drawn towards each other.

By the square cross-section of the bar, it can be achieved, that the supporting members can be arranged as mutually rotated over 90°. By the position of the bar in relation to the supporting member and the slot made in the supporting member, a strong connection between bar and supporting member can be obtained.

There is also the possibility, that with a corresponding square embodiment of the bar, a bush has been mounted in the sliding portion, with the axis of the bush being square to the axis of the bar and being in the same plane, in which bush a pressure element has been slidably received directly next to the bar, while screw thread has been made in the bush for receiving a bolt with which the pressure element can be pressed against the bar.

A clamping element having a screw therein running parallel to the axis of the bar can be mounted at every desired position on the bar by means of a snapping-clamping connection, for exerting a pressure or tensile force on a supporting member.

By the use of the snapping-clamping connection, such a clamping element can also be easily mounted between two supporting members already present on the bar. After the supporting members have been brought to and secured at the proper distance from each other, the clamping element can be removed, by which bearing the device will cause less problems with the patient.

A scale division can be made on the cleaning element, for measuring the distance across which a supporting member is moved with the help of the screw. This is particularly important, when two parts of a bone have to be brought at a certain distance from each other in order to grow together again.

Further, an auxiliary element can be mounted on the end of a screw directed towards the supporting member, of which auxiliary element the end surface turned away from the clamping element will come to lie against the supporting member, and in which auxiliary element a compression spring has been mounted, which forces the auxiliary element against the supporting member, with the pressure of the spring being controllable by means of the screw.

In this way, two parts of the bone connected to the device can be pressed against each other with a certain force.

According to another embodiment, it can also be provided for, that the screw fitted in the clamping element has been received in the screw thread of an adjusting sleeve surrounding the screw and being rotatable in the clamping element and having been locked in longitudinal direction by a set screw which is situated in an excavation in the adjusting sleeve, while the adjusting sleeve can be clamped by means of the set screw when the screw and by this the relating supporting member has been brought to the desired position on the bar by rotating the adjusting sleeve, the screw having been received in a threaded hole made in the supporting member concerned and the screw having been provided with a flattened part on which a scale division is situated.

A further possibility is that the screw received in the clamping element is rotatable therein and has been screwed into the related supporting member, with a disc being present on the screw at both sides of the clamping element, which disc is rotatable on the screw thread of the screw, while two pressure elements are present between both discs, which pressure elements are movably guided in a bore made in the clamping element and running parallel to the screw and are urged away from each other by a compression spring, with the ends of the pressure elements protruding from the bore having been provided with a conical portion, which can be received in suitable excavations in said discs.

In particular, almost all parts of the device will be made from plastic, so that they transmit X-rays and thus do not hinder making X-ray photographs. Moreover, in doing so, the weight of the device can be limited, so that the user experiences as little trouble as possible by it.

BRIEF DESCRIPTION OF THE DRAWINGS

The invention is further explained by way of examples, illustrated in the drawings.

In the drawings.

DETAILED DESCRIPTION OF THE INVENTION

Figure 2:
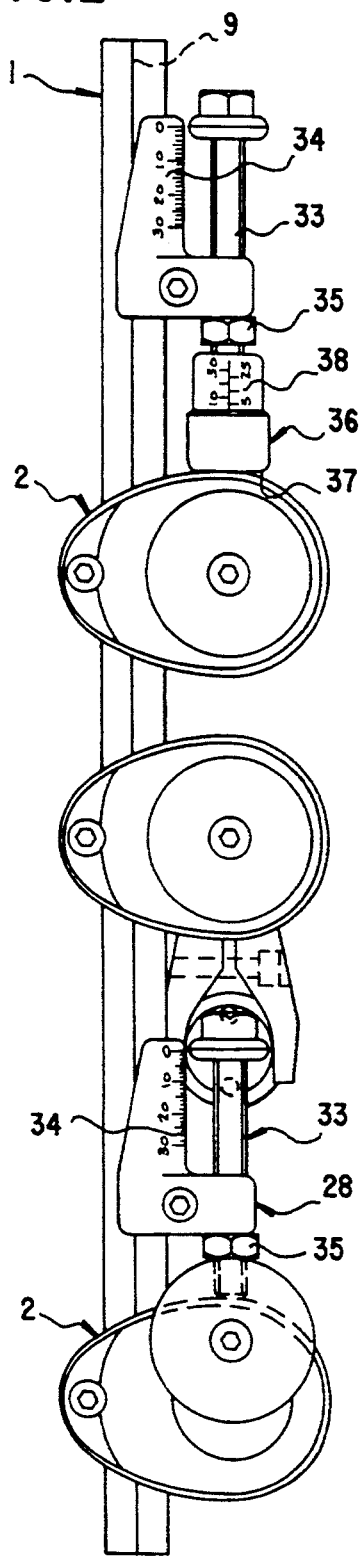
FIG. 2 shows a side view of the device according to FIG. 1, and that over an angle of 90° in relation to the side view of FIG. 1.

The device illustrated in the drawing comprises the bar 1, on which three supporting members 2 have been mounted. Each supporting member 2 consists of a sliding portion 3 with an opening 4 therein for passing a bar 1 and of a supporting plate 5 with an opening 6 therein through which a clamping bolt 7 can extend.

The sliding portion 3 has a slit 8 which extends to a longitudinal edge 9 of the bar 1, in such a way that the parts 10 are formed, which can be pulled towards each other by means of the bolt 11 in order to clamp the supporting member 2 on the bar 1.

The one surface 12 of the supporting plate 5 is convex and the other surface 13 is concave. Against the surface 12 lies a concave surface 14 of the ring 15. The head 16 of the bolt 7 bears against the other surface of the ring 14 and this bolt extends through the opening 17 of the ring 15 and the other end 18 thereof has been screwed into a threaded bore 19 of a receiving element 20. The receiving element 20 comprises a convex surface 21 which lies against the concave surface 13 of the supporting plate 5. The receiving element 20 has been provided with a number of bores 19, such that the receiving element 20 can take up very different positions in relation to the supporting member 2 and yet be fixedly clamped thereto. Owing to the square shape of the bar 1, the supporting member 2 can be fitted on the bar in various positions as well.

The receiving element 20 has been provided with a slot 22 and not further indicated excavations are situated in the opposing surfaces formed by the slot for receiving screws 23, which can be fitted in a part of a bone 24. The screws 23 are fixed in the receiving element 20 by the clamping bolts 25.

When it is possible, the center of the concave surface 13 and thus of the convex surface 21, will come to lie in the bone 24 and that as close as possible to the axis 26 thereof.

Figure 1:
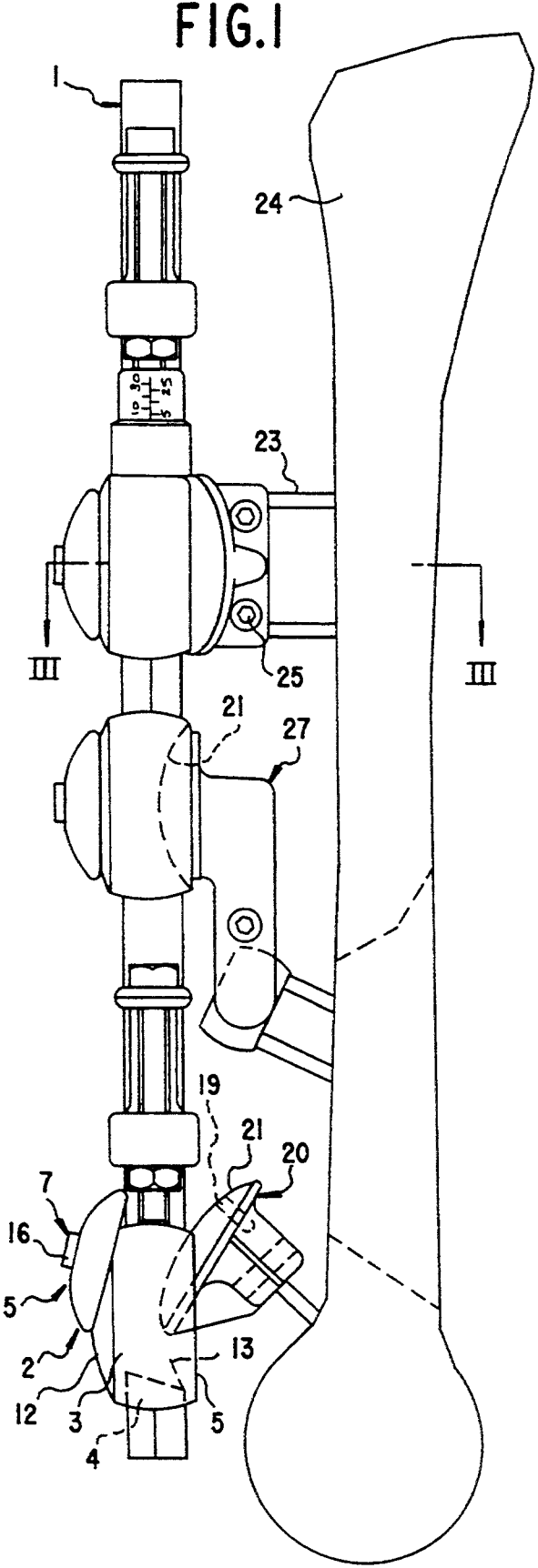
FIG. 1 shows a side view of a device according to the invention, in which a bone with which the device has been connected has also been illustrated.
Figure 3:
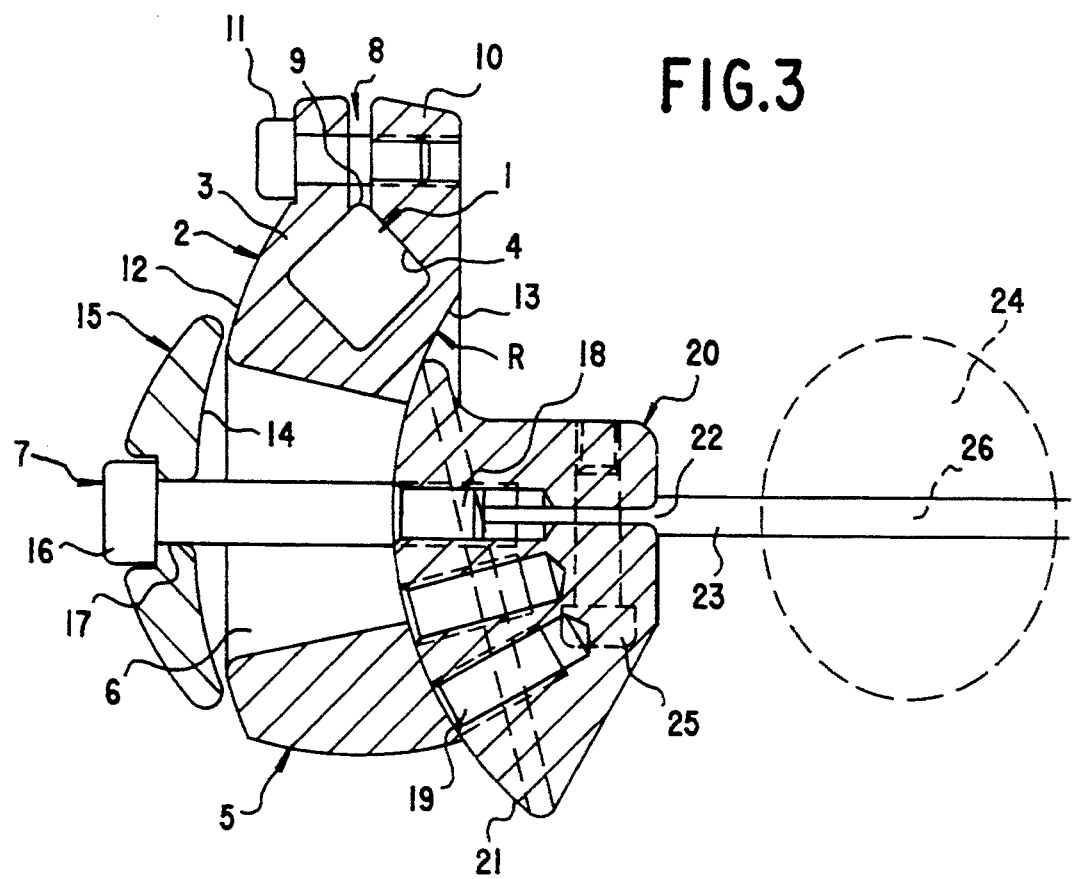
FIG. 3 shows a cross-section according to the line III—III of FIG. 1.

Further, the possibility of making a receiving element 27 from two parts has been indicated in FIGS. 1 and 2, namely from a first part, not further indicated, provided with the convex surface 21 and with a fork-like shape for supporting the second part, which carries the screws 23. The various parts can be fixed in relation to each other by clamping bolts not further indicated.

Figure 4:
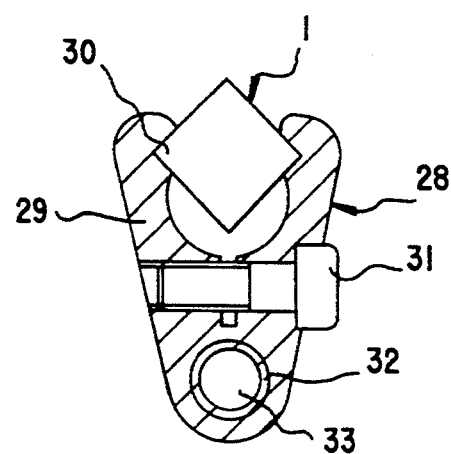
FIG. 4 shows an end view of a clamping element mounted on the bar.

FIG. 4 shows a view of a clamping element 28 which can also be mounted on the bar 1, as appears from FIGS. 1 and 2. The clamping element comprises the two legs 29 with recesses 30 in the ends thereof, which can embrace the bar 1, after which the clamping element 28 can be clamped on the bar 1 by means of the clamping bolt 31.

The clamping 28 has further been provided with the threaded bore 32 for receiving the screw 33. As appears from the lower part of FIGS. 1 and 2, the screw 33 can be tightened directly against a supporting member for moving this member on the bar 1. In this way, two bone portions can be brought at a distance from each other and this distance can be determined with the help of the scale division 34 on the clamping element 28. After adjustment of the screw 33, it can be fixed with the nut 35.

In the upper part of FIGS. 1 and 2 has been indicated, that an auxiliary element 36 can be present between the screw 33 and a supporting member 2, in which auxiliary element a spring—not further indicated—has been received, so that the end surface 37 of the auxiliary element can be pressed against the supporting member 2 with an adjustable force. The exerted force can be determined with the help of the scale division 38.

Figure 5:
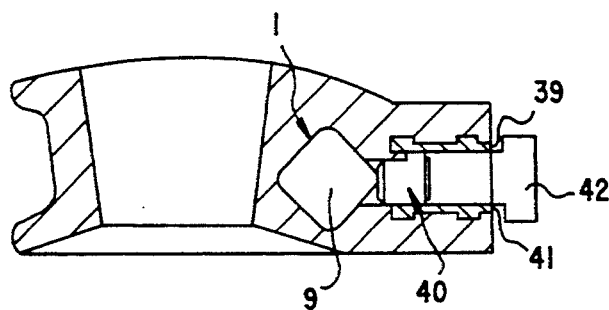
FIG. 5 shows a cross-section over a modified embodiment of a supporting member as shown in FIG. 3.

FIG. 5 shows a somewhat modified embodiment of the sliding portion 3 of a supporting member 2. Here-with, no slot 8 has been provided, but a bush 9 has been fixedly mounted in the sliding portion 3. A pressure element 40 has been slidably received in the bush 39. Further, screw thread 41 has been fitted in the bush 39, so that a screw 42 can be screwed into it, by which screw the pressure element 40 can be clamped against the bar 1. Thus, there will be no need to employ the resiliency of the material of the sliding portion 3.

Figure 6:
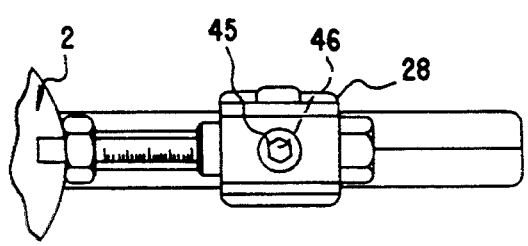
FIG. 6 shows a view of a modified embodiment of a device mounted on the bar for moving a supporting member along the bar.
Figure 7:
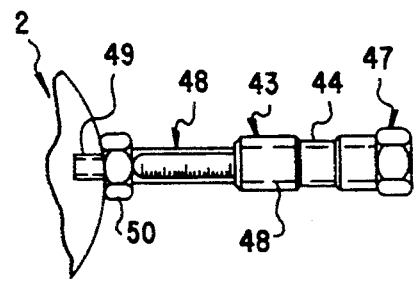
FIG. 7 shows a part of FIG. 6, but with omission of the clamping element mounted on the bar.

The FIGS. 6 and 7 show an embodiment in which a clamping element 28 to be secured on the bar 1 corresponds substantially to that shown in FIG. 4. Here, the bore 32 has not been provided with screw thread and an adjusting sleeve 43 is rotatable in this bore. In order to prevent axial movement of the adjusting sleeve 43 in the bore, it has been provided with a portion 44 of decreased diameter, in which a set screw 45 can be received, which has been fastened in a threaded bore 46 in the clamping element 28. For rotating the adjusting sleeve 43, it has been provided with a hexagon 47. An inner thread has been fitted in the adjusting sleeve 43 for receiving the screw 48, one end of which having been provided with screw thread 49 for securing a screw 48 in a supporting member 2 and locking it therein by means of the check nut 50. It will be obvious, that by rotating the adjusting sleeve 43, the screw 48 and with it the supporting member 2 can be moved along the bar 1. After bringing the supporting member in the desired position, the adjusting sleeve 43 can be secured in the clamping element 28 with the help of the set screw 45. On a flattened part of the screw 48, one can apply a scale division again.

Figure 8:
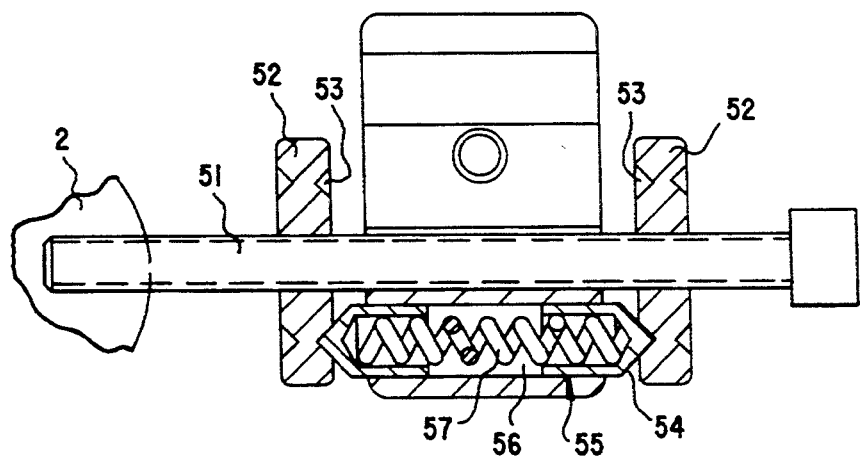
FIG. 8 diagrammatically shows a cross-section across yet another embodiment of a device mounted on the bar, for moving a supporting member along the bar and after that securing the supporting member on the bar.

FIG. 8 shows an embodiment in which once again a clamping element 28 is used with a non-threaded bore 32 in which a screw 51 has been rotatably received. The screw 51 has been connected to the supporting member 2. At both sides of the clamping element 28, a disc 52 provided with screw thread has been mounted on the screw 51. The discs 52 have been provided with conical recesses 53, in which the conical parts 54 of pressure elements 55 have been received. The pressure elements 55 have been received in a bore 56 in the clamping element 28 and are pushed away from each other by means of the spring 57. On rotating one disc 52 in relation to the other one, a pressure element 55 can snap into another recess 53, so that the discs 52 are retained in relation to each other.

It will be obvious, that only some possible embodiments of the device according to the invention have been illustrated in the drawing and described above, and that many modifications can be made, without falling beyond the inventive idea.

We claim:

1. Bone fixation device comprising a profiled bar on which at least two supporting members have been movably and lockably mounted, which supporting members have a sliding portion with an opening therein for passing the bar and onto which supporting members receiving elements can be clamped, each serving to receive at least one screw, which can be secured in one part of a bone wherein each supporting member comprises a supporting plate extending from the sliding portion of the supporting member situated on the bar, with one surface of the supporting plate being concave and the opposing surface being convex and with an opening made in each plate for passing a clamping bolt which extends through a ring having a concave surface lying flat against the convex surface of the supporting plate and which bolt has been screwed into one of a number of threaded bores made in a receiving element having a convex surface lying flat against the concave surface of the supporting plate.

2. A bone fixation device comprising:
a profiled bar;
at least two support members slidably mounted on said bar, each of said support members being comprised of a sliding portion having an opening therein for receiving said bar and a supporting plate having a first curved surface and an opening therein; and
a receiving element for receiving a screw secured in a bone fastened to each of said support members, said receiving element having a curved surface for mating with said first curved surface of said supporting plate and at least two bores therein, wherein said curved surface of said receiving element is fastened against said first curved surface of said supporting plate by a bolt secured in one of said bores in said receiving element, said bolt passing through said opening in said supporting plate.

3. The bone fixation device of claim 2, wherein said first curved surface of said supporting plate is concave and said curved surface of said receiving element is convex.

4. The bone fixation device of claim 3, wherein said supporting plate has a second curved surface opposite said first curved surface, said second curved surface being convex.

5. The bone fixation device of claim 4, wherein the device further comprises a ring having a concave surface, said ring being clamped against said supporting plate by said bolt so that said concave surface of said ring is pressed against said second curved surface of said supporting plate.

6. The bone fixation device of claim 2, wherein said bar has a square cross section and said sliding portion is divided into opposing portions by a slot extending therethrough and into said opening in said sliding portion, said opposing portions being clamped together by a bolt to slidably mount said supporting member on said bar.

7. The bone fixation device of claim 2, wherein said bar has a square cross section and said sliding portion further comprises a bushing mounted therein, a pressure element slidably disposed in said bushing, and a screw for clamping said pressure element against said bar to slidably mount said supporting member on said bar.

8. The bone fixation device of claim 7, wherein an axis of said bushing is perpendicular to an axis of said bar.

9. The bone fixation device of claim 2, wherein said first curved surface of said supporting plate is concave and a center of curvature of said first curved surface intersects with a portion of bone connected to said device.

10. The bone fixation device of claim 4, wherein said supporting plate extends from said sliding portion so that planes defined by edges of said opening in said supporting plate at said first and second curved surfaces are situated at opposing sides of an axis of said bar.

11. The bone fixation device of claim 2, further comprising a clamping element mounted on said bar, said clamping element having a screw disposed therein for exerting a force on a supporting member, said screw being disposed parallel to an axis of said bar.

12. The bone fixation device of claim 11, further comprising an auxiliary element mounted on an end of said screw disposed in said clamping element so that an end surface of said auxiliary element is adjacent to a supporting member, said auxiliary element having a compression spring mounted therein for forcing said auxiliary element against said supporting member, wherein spring pressure of said spring is controllable by means of said screw.

13. The bone fixation device of claim 11, wherein said screw is disposed in an adjustable sleeve rotatably disposed in a bore in said clamping element, said adjustable sleeve being secured in said clamping element by a set screw.

14. The bone fixation device of claim 13, wherein said screw has a flattened portion on which a scale division is provided.

15. The bone fixation device of claim 11, wherein said screw extends through a first bore in said clamping element and is connected to a supporting member, and said device further comprises a pair of discs rotatably mounted on said screw on opposing sides of said clamping element, said discs having conical recesses therein, a pair of pressure elements having conical end portions, said pressure elements being disposed in a second bore in said clamping element, said second bore being parallel to said screw, said pressure elements being urged away from each other by a compression spring so that said conical end portions of said pressure elements protrude from opposite ends of said second bore and are received in said conical recesses in said discs.

16. The bone fixation device of claim 2, wherein said profiled bar, said support members, and said receiving elements are made of plastic.

* * * * *